United States Patent [19]

Röeschlau et al.

[11] 3,948,728

[45] Apr. 6, 1976

[54] STEROID-Δ-ISOMERASE

[75] Inventors: Peter Röeschlau; Gunter Lang; Klaus Beaucamp, all of Tutzing, Upper Bavaria; Erich Bernt, Munich, all of Germany

[73] Assignee: Boehringer Mannheim G.m.b.H., Mannheim-Waldhof, Germany

[22] Filed: Apr. 9, 1975

[21] Appl. No.: 566,481

[30] Foreign Application Priority Data
Apr. 19, 1974 Germany............................ 2418978

[52] U.S. Cl........... 195/62; 195/66 R; 195/103.5 R; 195/51 R
[51] Int. Cl.² C07G 7/028; C12D 13/10; C12K 1/00
[58] Field of Search............. 195/51 R, 103.5 R, 62, 195/66 R

[56] References Cited
OTHER PUBLICATIONS
Alfsen et al., Biochem. and Biophys. Res. Comm., Vol. 20, pp. 251–255, (1965).

*Primary Examiner*—Lionel M. Shapiro
*Attorney, Agent, or Firm*—Burgess, Dinklage & Sprung

[57] ABSTRACT

The new enzyme steroid-Δ-isomerase is provided, as well as a process for producing same, comprising digesting a micro-organism containing said isomerase, extracting same by destruction of the cell wall with a buffer solution containing a non-ionic surfactant, centrifuging the resulting mass and discarding the precipitate, applying the extract to an anion exchanger, eluting the enzyme with a buffer solution containing a non-ionic surfactant, heating the eluate, separating the precipitate and isolating the enzyme therefrom from the supernatant.

20 Claims, No Drawings

STEROID-DELTA-ISOMERASE

The present invention relates to a new enzyme, steroid-Δ-isomerase, and with the preparation thereof.

A 3-ketosteroid-$\Delta^4,\Delta^5$-isomerase (designated EC 5.3.3.1) is already known. This enzyme is a $C_{19}$- and $C_{21}$-isomerase. The substrates for this enzyme are $\Delta^5$-androsten-3,17-dione and $\Delta^5$-pregnen-3,20-dione. However, $\Delta^5$-cholesten-3-one is not a substrate therefor.

A 3-keto-cholesten-$\Delta^5,\Delta^4$-isomerase is also known (see Alfsen et al., Biochem. and Biophys. Res. Comm., 20, 1965). This is a $C_{27}$-isomerase for which $\Delta^5$-cholesten-3-one serves as a substrate but not $\Delta^5$-androsten-3,17-dione and $\Delta^5$-pregnen-3,20-dione.

In contradistinction thereto, the present invention provides a new steroid-Δ-isomerase which is not only a $C_{19}$- and $C_{21}$-isomerase but also a $C_{22}$-isomerase.

Thus, the present invention provides a steroid-Δ-isomerase which is characterized by a maximum activity at pH 7.5 to 8.0, a Michaelis constant $K_m[M]$ of $2.7 \times 10^{-4}$ with regard to $\Delta^5$-cholesten-3-one, of $2.5 \times 10^{-4}$ with regard to $\Delta^5$-pregnen-3,20-dione and of $2.2 \times 10^{-4}$ with regard to $\Delta^5$-androsten-3,17-dione, measured in phosphate buffer at pH 7.5 at an optimum ionic strength of 0.4 to 0.6M and by being activatable by surface-active materials or phosphate buffer.

Therefore, the new enzyme according to the present invention catalyzes, quite generally, the conversion of 3-keto-$\Delta^5$-steroids into 3-keto-$\Delta^4$-steroids.

The following Table 1 illustrates the ability of the enzyme to be activated by various buffers:

TABLE 1

| 0.5M buffer, pH 7.5 | activation factor |
|---|---|
| HCl - triethanolamine | 1 |
| HCl - tris-(hydroxymethyl)-aminomethane | 2.8 |
| sodium phosphate | 130 |

The new enzyme according to the present invention is also activated by surface-active materials (detergents) as is shown by the following Table 2:

TABLE 2

| surface-active agent | activation factor |
|---|---|
| without | 1 |
| 0.1% hydroxypolyethoxy-dodecane | 4.4 |
| 0.05% sodium desoxycholate | 13.2 |
| 0.1% octyl-phenol-polyethylene glycol ether | 46.1 |

The molecular weight of the new enzyme according to the present invention was determined as being about 60,000. The enzyme proved to be stable at pH values between 4 and 6.

The following Table 3 shows the heat-stability properties of the new enzyme:

TABLE 3

| period of heating (minutes) | temperature (°C.) | loss of activity (%) |
|---|---|---|
| 5 | 70 | 56 |
| 5 | 75 | 70 |

The new enzyme according to the present invention can be precipitated by ammonium sulfate at concentrations of between 1 and 1.9M.

The new enzyme according to the present invention can be prepared by digesting or extracting a micro-organism which has a sufficient content of steroid-Δ-isomerase to make it worthwhile to work up, by destruction of the cell walls with a buffer solution containing a non-ionic, surface-active agent, applying the extract, after centrifuging and discarding the precipitate thereby obtained, to an anion exchanger, eluting the enzyme with a buffer solution containing the non-ionic, surface-active agent, subjecting the eluate to a heating step, discarding the precipitate thereby obtained and isolating the enzyme in known manner from the supernatant.

Before destruction of the cell wall, the micro-organism is preferably washed with a mixture of butanol and water.

After digestion of the micro-organism, the enzyme is preferably precipitated from the extract by the addition of ammonium sulfate and thereafter again taken up in buffer solution.

For the elution of the anion exchanger, there is preferably used a 0.01 to 0.2 molar buffer solution containing the surface-active agent.

The eluate is preferably adjusted to an ammonium sulfate concentration of 0.65 to 0.85M and subsequently heated at a pH value between 3.0 and 4. Under the given conditions, a period of heating of 15 minutes at 25°C. has proved to be suitable. In the case of a corresponding shortening of the period of heating, it is possible to heat to a higher temperature. The period of heating which is suitable at a particular pH value and at a particular temperature can easily be determined, from case to case, by a few experiments.

The precipitate which is formed by the heating step is separated off, perferably by centrifuging, and the enzyme is isolated from the supernatant. For the removal of the ions, it is thereby preferable first to dialyze, then again to remove the enzyme from the dialyzate bound to an anion exchanger and thereafter to repeat the elution step. The purified enzyme thus obtained still contains surface-active agent which, if desired, can be removed, for example, by means of a molecular sieve material.

As starting materials for obtaining the new enzyme according to the present invention, there can be used, as already mentioned, micro-organisms with a content of steroid-Δ-isomerase which is sufficient to make recovery worthwhile. Micro-organisms are preferably employed which are able to utilize steroids, for example, those which have been cultured using steroids, such as cholesterol, as the source of carbon. Examples of such micro-organisms include Nocardia erythropolis NCIB 9158, ATCC 17895 and ATCC 4277 and Nocardia formica ATCC 14811. However, for the production of the new enzyme according to the present invention, other micro-organisms, bacteria and fungi can also be employed.

The digestion of the micro-organisms by destruction of the cell wall by means of detergents is known and, in principle, all the methods previously described for this purpose and already used in practice can be employed.

Preferred non-ionic, surface-active agents for this digestion include the alkyl-aryl-ethylene-glycols and polyethylene oxide-polypropylene oxide adducts, especially the esters thereof. The concentration of the surface-active agent to be used in the buffer solution employed for the digestion and extraction of the enzyme depends, to a certain extent, upon the actual surface-active agent used and can be determined by preliminary experiments. In general, concentrations of between about 0.01 and 3% and preferably of between 0.1 and 1%, can be used. The buffer solution used can have a pH value between about 4 and 9 and preferably of between 5 and 8.

Particularly good results are obtained when the micro-organism, before the digestion and extraction, is subjected to a washing with a mixture of butanol and water in the presence of the surface-active agent. In this way, the extractable activity during the course of the subsequent digestion can be increased. The washing with butanol-water can be carried out in one or more steps.

The extract obtained by the digestion, which contains the steroid-$\Delta$-isomerase dissolved therein, is subsequently purified by means of anion exchangers. The combined use of buffer salts and surface-active agent has proved to be very suitable for the elution.

The preferred anion exchangers are the weakly basic types, for example exchangers containing diethylaminoethanol groups.

The elution of the anion exchanger is preferably carried out with a 0.01 to 0.2 molar buffer solution of the above-mentioned pH range. The concentration of the surface-active agent is then preferably within the range of from 0.05 to 2%. The use of 0.03 to 0.1 molar phosphate buffer with a content of 0.2 to 0.7% surface-active, non-ionic agent is especially preferred.

The eluate is preferably adjusted to an ammonium sulfate concentration of 0.7 to 0.8M and cooled to 0°C. A pH value of 3 to 4 and preferably of 3.1 to 3.5 is then preferably adjusted by the addition of a dilute acid, preferably of hydrochloric acid, followed by warming to a temperature of from 25° to 40°C. for a period of from 15 to 3 minutes. After separation of the precipitate which is thereby obtained, the enzyme can be isolated from the solution in the usual manner, for example, by precipitation with salts, for example ammonium sulfate, or by organic solvents, for example, methanol.

The enzyme according to the present invention can be used in practice for the determination of 3-keto-$\Delta^5$-steroids. These substrates are very quickly converted by the enzyme according to the present invention into the corresponding $\Delta^4$-steroids which are characterized by an outstanding UV absorption and can, therefore, easily be determined quantitatively at 240 nm. This rearrangement takes place in about 1 to 2 minutes in the presence of the new enzyme according to the present invention, whereas, in the absence of the enzyme, the rearrangement requires several hours.

The following Examples are given for the purpose of illustrating, without limitation, the present invention:

EXAMPLE 1

40 ml. of a suspension of *Nocardia erythropolis* ATCC 4277 (about 10 g. dry weight) were mixed with 40 ml. n-butanol and was stirred for a few minutes at ambient temperature. The mixture centrifuged and the butanol, as well as the supernatant aqueous phase, were poured away. The precipitate was again mixed with 40 ml. water and, after the production of a homogeneous suspension of the cells, again mixed with 40 ml. n-butanol, stirred for a few minutes at ambient temperature and centrifuged. The precipitate was suspended in 40 ml. 0.01 molar phosphate buffer (pH 7.0) to which had been added a non-ionic, surface-active agent (alkyl-aryl-polyethylene-glycol) and stirred at ambient temperature for 30 minutes. The mixture was subsequently centrifuged and the precipitate discarded.

This extract was mixed with solid ammonium sulfate at 0°C. up to a concentration of 1.3M ammonium sulfate. The suspension was subsequently centrifuged, whereby the separated material collected on the surface of the solution, presumably because of the lipophilic component thereof. The coagulated material was filtered off, dissolved with 0.01 molar phosphate buffer (pH 7) and subsequently exhaustively dialyzed against the same buffer at 0°C.

The dialyzed solution was applied to a column of a commercially available anion exchanger containing diethylaminoethanol groups and based on dextran which had been equilibrated with 0.01 molar phosphate buffer (pH 7), the enzyme thereby being adsorbed. After washing the column with the same buffer, it was subsequently washed successively with aqueous solutions containing 0.5%, 2% and 5% of the above-mentioned surface-active agent, large amounts of impurities thereby being eluted. Subsequently, the column was washed successively with 0.01M phosphate buffer (pH 7), 0.05M phosphate buffer (pH 7), 0.2M phosphate buffer (pH 7) and 0.05M phosphate buffer (pH 7), whereafter the desired enzyme was eluted with 0.05 molar phosphate buffer to which had been added 0.5% surface-active agent.

The eluate was adjusted to an ammonium sulfate concentration of 0.75M and mixed with a further 1% of the surface-active agent. It was then cooled to 0°C. in an icebath and adjusted to a pH value of 3.2 with 0.2N hydrochloric acid. Subsequently, it was heated to 25°C. The precipitate formed was centrifuged off and the supernatant adjusted to pH 6.0 with 0.2N aqueous sodium hydroxide solution and exhaustively dialyzed against 0.01M phosphate buffer (pH 6.0). 5% of a commercially-available anion exchanger containing diethylaminoethanol groups and based on dextran was added to the dialyzate and the exchanger subsequently filtered off. Subsequently, the exchanger was again eluted with 0.05M phosphate buffer (pH 6.0) to which had been added 0.5% of the surface-active agent. The new enzyme was present in the eluate with a specific activity of 120 to 170 U/mg. protein.

For the determination of activity, 3.0 ml. 0.5M potassium phosphate buffer (pH 7.5), 0.4% hydroxypolyethoxydodecane and 0.1 ml. of a $\Delta^5$-cholesten-3-one solution (obtained by dissolving 400 mg. $\Delta^5$-cholesten-3-one in 10 g. hydroxy-polyethoxy-dodecane and making up to 100 ml. with water) were mixed and 0.02 ml. of the eluate obtained as described above mixed therewith. The formation of the $\Delta^4$-cholesten-3-one was measured at 240 nm ($\epsilon = 15.5$ cm$^2$/$\mu$ Mol) as an increase of extinction per minute.

EXAMPLE 2

Determination of $\Delta^5$-cholesten-3-one 200 mg. $\Delta^5$-cholesten-3-one were dissolved in 10 g. hydroxypolyethoxydodecane and made up to 100 ml. with water. 0.01 ml. of this solution was added to 3.0 ml. 0.5M potassium phosphate buffer (pH 7.5) which contained 0.4% hydroxy-polyethoxydodecane. The extinction ($E_1$) was read off at 240 nm in a suitable spectrophotometer and the reaction started with 0.02 ml. (= 1.0 U) of steroid-Δ-isomerase. After 2 minutes, the extinction ($E_2$) was again read off. The concentration of the $\Delta^4$-cholesten-3-one and thus of the $\Delta^5$-cholesten-3-one was given from the difference between the first and the second reading, having regard to the molar extinction coefficient for $\Delta^4$-cholesten-3-one at 240 nm ($\epsilon = 15.5$ cm$^2$/μMol).

It will be understood that the specification and examples are illustrative but not limitative of the present invention and that other embodiments within the spirit and scope of the invention will suggest themselves to those skilled in the art.

What is claimed is:

1. Steroid-Δ-isomerase, characterized by:
   a. a maximum activity at pH 7.5 to 8.0,
   b. a Michaelis constant $K_m$ [M] of $2.7 \times 10^{-4}$ with regard to $\Delta^5$-cholesten-3-one, of $2.5 \times 10^{-4}$ with regard to $\Delta^5$-pregen-3,20-dione and of $2.2 \times 10^{-4}$ with regard to $\Delta^5$-androsten-3,17-dione, measured in phosphate buffer of pH 7.5 at an optimum ionic strength of 0.4 to 0.6M and
   c. being activatable by surface-active materials or phosphate buffer.

2. Process for producing steroid-Δ-isomerase as claimed in claim 1 which process comprises:
   digesting a micro-organism containing said isomerase,
   extracting same by destruction of the cell wall with a buffer solution containing a non-ionic surfactant,
   centrifuging the resulting mass and discarding the precipitate,
   applying the extract to an anion exchanger,
   eluting the enzyme with a buffer solution containing a non-ionic surfactant,
   heating the eluate,
   separating the resulting precipitate, and
   isolating the enzyme from the supernatant.

3. Process as claimed in claim 2, wherein the micro-organism is washed with a mixture of butanol and water prior to destruction of the cell wall.

4. Process as claimed in claim 2, wherein the enzyme is precipitated from the extract by adding ammonium sulfate and taking up the precipitate in buffer solution.

5. Process as claimed in claim 2, wherein said anion exchanger is eluted with 0.01 to 0.2 molar buffer solution containing the surfactant.

6. Process as claimed in claim 2, wherein the eluate is adjusted to an ammonium sulfate concentration of 0.65 to 0.86M and subsequently heated at a pH value of between 3.0 and 4.

7. Process as claimed in claim 2, wherein the micro-organism used is *Nocardia erythropolis* NCIB 9158, ATCC 17895 or ATCC 4277 or *Nocardia formica* ATCC 14811.

8. Process as claimed in claim 2, wherein the non-ionic surfactant is an alkyl-aryl-ethylene glycol or a polyethylene oxide-polypropylene oxide adduct or an ester thereof.

9. Process as claimed in claim 2, wherein the concentration of the non-ionic, surface-active agent in the buffer solution used for the digestion and extraction is between 0.01 and 3%.

10. Process as claimed in claim 9, wherein the concentration of the non-ionic, surface-active agent in the buffer solution is between 0.1 and 1%.

11. Process as claimed in claim 2, wherein the buffer solution used for the digestion and extraction has a pH value between 4 and 9.

12. Process as claimed in claim 11, wherein the buffer solution has a pH value between 5 and 8.

13. Process as claimed in claim 2, wherein the elution is carried out with a 0.01 to 0.2 molar buffer solution.

14. Process as claimed in claim 2, wherein the buffer solution used for the elution contains 0.05 to 2% of surface-active agent.

15. Process as claimed in claim 14, wherein the elution is carried out with a 0.03 to 0.1 molar phosphate buffer with a content of 0.2 to 0.7% surfactant, non-ionic agent.

16. Process as claimed in claim 2, wherein the eluate is adjusted to an ammonium sulfate concentration of 0.7 to 0.8M, cooled to 0°C. and the pH value adjusted to 3 to 4 by the addition of a dilute acid, followed by warming to a temperature of 25° to 40°C. for a period of from 15 to 3 minutes.

17. Process as claimed in claim 16, wherein the pH value is adjusted to 3.1 to 3.5.

18. Process as claimed in claim 16, wherein the dilute acid used is hydrochloric acid.

19. Process as claimed in claim 2, wherein the enzyme is finally isolated by precipitation with a salt or organic solvent.

20. Process for the determination of 3-keto-$\Delta^5$-steroids comprising converting said steroid to the corresponding 3-keto-$\Delta^4$-steroid with the enzyme claimed in claim 1 and measuring the UV adsorption of said converted steroid at 240nm.

* * * * *